United States Patent
Harling et al.

(10) Patent No.: US 10,336,744 B2
(45) Date of Patent: Jul. 2, 2019

(54) IAP E3 LIGASE DIRECTED PROTEOLYSIS TARGETING CHIMERIC MOLECULES

(71) Applicant: GlaxoSmithKline Intellectual Property Development Limited, Brentford, Middlesex (GB)

(72) Inventors: John David Harling, Stevenage (GB); Ian Edward David Smith, Stevenage (GB)

(73) Assignee: GlaxoSmithKline Intellectual Property Development Limited, Brentford, Middlesex (GB)

(*) Notice: Subject to any disclaimer, the term of this patent is extended or adjusted under 35 U.S.C. 154(b) by 0 days.

(21) Appl. No.: 15/568,006

(22) PCT Filed: Apr. 20, 2016

(86) PCT No.: PCT/EP2016/058769
§ 371 (c)(1),
(2) Date: Oct. 20, 2017

(87) PCT Pub. No.: WO2016/169989
PCT Pub. Date: Oct. 27, 2016

(65) Prior Publication Data
US 2018/0118733 A1  May 3, 2018

(30) Foreign Application Priority Data
Apr. 22, 2015  (GB) .................................. 1506871.1

(51) Int. Cl.
C07D 417/14  (2006.01)
A61K 31/4725  (2006.01)
A61K 31/519  (2006.01)
C07D 417/12  (2006.01)
C07D 487/04  (2006.01)
A61K 47/54  (2017.01)
A61K 47/66  (2017.01)

(52) U.S. Cl.
CPC ........ *C07D 417/14* (2013.01); *A61K 31/4725* (2013.01); *A61K 31/519* (2013.01); *A61K 47/545* (2017.08); *A61K 47/66* (2017.08); *C07D 417/12* (2013.01); *C07D 487/04* (2013.01)

(58) Field of Classification Search
None
See application file for complete search history.

(56) References Cited

U.S. PATENT DOCUMENTS

2014/0057924 A1  2/2014  Wang et al.

FOREIGN PATENT DOCUMENTS

| CN | 105 085 620 | 11/2015 |
|---|---|---|
| WO | WO 2013/106643 A2 | 7/2013 |
| WO | WO 2014/055461 A1 | 4/2014 |

OTHER PUBLICATIONS

Itoh, Y, J, Amer Chem Soc 2010 vol. 132 pp. 5820-5826.*
Itoh, Y. et al., J. Amer. Chem. Soc. 2010, vol. 132, pp. 5820-5826.*
Daniel P. Bondeson et al., Catalytic in vivo protein knockdown by small-molecule Protac, Nature Chemical Biology, vol. 11, No. 8, Jun. 10, 2015, pp. 611-617, ISSN: 1552-4450.
Dennis L. Buckley, et al: Small-Molecule Control of Intracellular Protein Levels through Modulation of the Ubiquitin Proteasome System, Angewandte Chemie International Edition, vol. 53, No. 9, Jan. 23, 2014 (Jan. 23, 2014), pp. 2312-2330, ISSN: 1433-7851.
Jin Meizhong et al: 11 Abstract LB-097: Targeted degradation of the androgen receptor in prostate cancer 11, AACR Meeting 2015, Apr. 20, 2015 (Apr. 20, 2015), XP55279137, Retrieved from the Internet: URL:http://www.abstractonline.com/Plan/ViewAbstract.aspx?mID=3682&sKey=9924d266-b02b-4375-b036-a096d1fbae16&cKey=1c8644c3-9595-4d3c-be4d-79cf1c8d037b&mKey=19573a54-ae8f-4e00-9c23-bd6d62268424 [retrieved on Jun. 9, 2016] & Meizhong Jin et al: 11 Targeted Degradation of the Androgen Receptor in Prostate Cancer 11, AACR Meeting 2015, Abstract 8924/LB-097, Apr. 20, 2016.
Lu Jing, Hijacking the E3 ubiquitin ligase cereblon to create efficient BRD4 degraders, AACR Meeting 2015, LB-010, Apr. 19, 2015 (Apr. 19, 2015), XP55279089, Retrieved from the Internet: URL:http://www.abstractonline.com/Plan/ViewAbstract.aspx?mID=3682&sKey=5cl3fed6-b362-48b8-b68b-la30ce228c&cKey=bd034c46-ffbc-4b51-9bce-f alelb096ae5&mKey=I9573a54-ae8f-4e00-9c23-bd6d62268424 [retrieved on Jun. 9, 2016] the whole document—& Jing Lu et al: "Hijacking the E3 Ubiquitin Ligase Cereblon to Efficiently Target BRD4", AACR Meeting 2015, LB-010, Apr. 19, 2015 (Apr. 19, 2015), pp. 1-1.
M. Mingozzi, et al., Synthesis and biological evaluation of dual action cyclo-RGD/SMAC mimetic conjugates targeting [alpha]v[beta]3/[alpha]v[beta]5 integrins and IAP proteins, Organic & Biomolecular Chemistry, vol. 12, No. 20, Jan. 1, 2014 (Jan. 1, 2014), p. 3288, ISSN: 1477-0520.
Min Zhuang et al., Substrates of IAP Ubiquitin Ligases Identified with a Designed Orthogonal E3 Ligase, the NEDDylator, Molecular Cell., vol. 49, No. 2, Jan. 1, 2013, pp. 273-282, ISSN: 1097-2765.
Qian Cai, et al., A Potent and Orally Active Antagonist (SM-406/AT-406) of Multiple Inhibitor of Apoptosis Proteins (IAPs) in Clinical Development for Cancer Treatment, Journal of Medicinal Chemistry, vol. 54, No. 8, Apr. 28, 2011 (Apr. 28, 2011), pp. 2714-2726, XP055084190, ISSN: 0022-2623.
Schneekloth A R et al., Targeted intracellular protein degradation induced by a small molecule: En route to chemical proteomics, Bioorganic & Medicinal Chemistry Letters, Pergamon, Amsterdam, NL, vol. 18, No. 22, Nov. 15, 2008 (Nov. 15, 2008), pp. 5904-5908, ISSN: 0960-894X.
Yukihiro Itoh, et al., Protein Knockdown 1-14 Using Methyl Bestatin-Ligand Hybrid Molecules: Design and Synthesis of Inducers of Ubiquitination-Mediated Degradation of Cellular Retinoic Acid-Binding Proteins, Journal of the American Chemical Society, vol. 132. No. 16, Apr. 28, 2010 (Apr. 28, 2010), pp. 5820-5826, ISSN: 0002-7863.
Yukihiro Itoh, et al., Design, synthesis and biological evaluation of nuclear receptor-degradation inducers, Bioorganic & Medicinal Chemistry, Pergamon, GB, vol. 19, No. 22, Sep. 22, 2011 (Sep. 22, 2011), pp. 6768-6778, ISSN: 0968-0896.

* cited by examiner

*Primary Examiner* — Heidi Reese
(74) *Attorney, Agent, or Firm* — Nora L. Stein; Fang Qian; Edward R. Gimmi

(57) ABSTRACT

The present invention relates to compounds, compositions, combinations and medicaments containing said compounds and processes for their preparation. The invention also relates to the use of said compounds, combinations, compositions and medicaments, for example as inhibitors of the activity of RIP2 kinase, including degrading RIP2 kinase, the treatment of diseases and conditions mediated by the RIP2 kinase, in particular for the treatment of inflammatory diseases or conditions.

2 Claims, No Drawings

IAP E3 LIGASE DIRECTED PROTEOLYSIS TARGETING CHIMERIC MOLECULES

This application is a 371 of International Application No. PCT/EP2016/058769, filed 20 Apr. 2016, which claims benefit to Application No. GB 1506871.1 filed 22 Apr. 2015. The entire teachings of the above identified applications are incorporated herein by reference.

FIELD OF THE INVENTION

The present invention relates to compounds, compositions, combinations and medicaments containing said compounds and processes for their preparation. The invention also relates to the use of said compounds, combinations, compositions and medicaments, for example as inhibitors of the activity of target proteins, including degrading target proteins and the treatment of diseases and conditions mediated by the target proteins.

BACKGROUND OF THE INVENTION

The selective degradation of target proteins using small molecules is a new approach to the treatment of various diseases. Proteolysis Targeting Chimeric molecules (Protacs) are bifunctional molecules which can simultaneously bind a target protein and an E3 ubiquitin ligase thereby bringing the ligase and target in close proximity These bifunctional molecules allow the efficient ubiquitin transfer from the ligase complex to the target protein which is subsequently recognized by the proteasome and degraded. This degradation of the target protein provides treatment of diseases or conditions modulated through the target protein by effectively lowering the level of said target protein in the cells of the patient. An advantage of Protacsis that a broad range of pharmacological activities is possible, consistent with the degradation/inhibition of targeted proteins from virtually any class or family.

E3 ubiquitin ligases (of which hundreds are known in humans) confer substrate specificity for ubiquitination and therefore are more attractive therapeutic targets than general proteasome inhibitors due to their specificity for certain protein substrates. The development of ligands for E3 ligases has proven challenging. One suitable E3 ubiquitin ligase is the von Hippel-Lindau tumour suppressor (VHL), see for example WO2013/106643.

It would be desirable to identify further E3 ubiquitin ligase binding molecules to incorporate into Protac molecules.

Protacs employed to target proteins to the E3 ligase IAP (Inhibitors of Apoptosis) through the ligand bestatin have been proposed with limited success, see for example Ohoka et al, Cell Death and Disease, 2014, 5, e1513. Unfortunately bestatin is a non-specific ligand with multiple activities. IAP inhibitors are known which can be of use in their own right as antitumour agents, see for example L. Bai et al./Pharmacology & Therapeutics 144 (2014) 82-95 Apoptosis is one form of programmed cell-death and is a normal cellular process used by multi-cellular organisms to eliminate damaged or unwanted cells. Apoptosis is a tightly regulated process and faulty regulation of apoptosis is implicated in many human diseases, including cancer, autoimmune diseases, inflammation, and neurogenesis (Lowe S. W and Lin 2000 Carcinogenesis 21(3), 485-495, Nicholson D. W. 2000, Nature 407 (6805) 810-816, Reed J. C. 2002 Nat Rev Drug Discovery 1(2) 111-121).

Selective IAP inhibitors are disclosed, for example in WO 2014031487 WO 2014047024 which describe linked dimeric compounds. WO 2014055461 describes bivalent compounds and WO 2008128171, WO2008/016893, WO 2014/060768, WO2014/060767, and WO15092420 describe IAP inhibitors all with a view to treating disorders associated with apoptosis, particularly cancer.

The present inventors have identified E3 ligase IAP inhibitor compounds which when incorporated into Protacs as the "degradation component", including Protacs targeting RIP2 Kinase, BTK and the estrogen receptor are capable of promoting target degradation.

SUMMARY OF THE INVENTION

The present invention provides Protac compounds incorporating a selective E3 Ligase IAP binding moiety (IAP binding moiety) as the degradation component, functioning to recruit target proteins to the E3 ubiquitin ligase IAP for degradation In a first aspect, the present invention provides a selective IAP binding moiety together with a linker In a further aspect there is provided a compound of Formula (I);

Target Protein Binder-Linker-IAP binder     (I)

or a pharmaceutically acceptable salt thereof

In a further aspect of the present invention, there is provided a compound of formula (I) or a pharmaceutically acceptable salt thereof for use in therapy.

In a further aspect there is provided a compound of formula (I) or a pharmaceutically acceptable salt thereof for use in the treatment of diseases conditions mediated by the target protein.

In a further aspect of the present invention, there is provided a pharmaceutical composition comprising a compound of formula (I) or a pharmaceutically acceptable salt thereof and one or more of pharmaceutically acceptable carriers, diluents and excipients.

In a further aspect of the present invention, there is provided a method of treating diseases and conditions mediated by the target protein in a subject comprising administering a therapeutically effective amount of a compound of formula (I) or a pharmaceutically acceptable salt thereof.

In a further aspect of the present invention, there is provided the use of a compound of formula (I), or a pharmaceutically acceptable salt thereof in the manufacture of a medicament for use in treating diseases and conditions mediated by the target protein.

In a further aspect there is provided a combination comprising a compound of formula (I), or a pharmaceutically acceptable salt thereof and at least one further therapeutic agent.

In a further aspect there is provided a combination comprising a compound of formula (I) or a pharmaceutically acceptable salt thereof and at least one further therapeutic agent for use in therapy.

In a further aspect of the present invention, there is provided a pharmaceutical composition comprising a combination comprising a compound of formula (I) or a pharmaceutically acceptable salt thereof and at least one further therapeutic agent and one or more of pharmaceutically acceptable carriers, diluents and excipients.

In a further aspect of the invention there is provided a combination comprising compound of formula (I) or a pharmaceutically acceptable salt thereof and at least one further therapeutic agent for use in treating diseases and conditions mediated by the target protein.

In a further aspect there is provided a method of treating diseases and conditions mediated by the target protein comprising administering to a human in need thereof a therapeutically effective amount of a combination comprising compound of formula (I) or a pharmaceutically acceptable salt thereof, and at least one further therapeutic agent.

In a further aspect there is provided the use of a combination comprising compound of formula (I) or a pharmaceutically acceptable salt thereof and at least one further therapeutic agent in the manufacture of a medicament for treating diseases and conditions mediated by the target protein.

In a further aspect there is provided a method of degrading the target protein comprising administering to a human in need thereof a therapeutically effective amount of a compound of Formula (I) or a pharmaceutically acceptable salt thereof

DETAILED DESCRIPTION OF THE INVENTION

As used herein, "a compound of the invention" includes all solvates, complexes, polymorphs, radiolabelled derivatives, stereoisomers, tautomers and optical isomers of the compounds of formula (I) and salts thereof.

As used herein, a "selective IAP inhibitor" is a compound which is selective for the BIR2 and BIR3 domains of the IAP family of proteins.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of formula (I) may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

It is also noted that the compounds of formula (I) may form tautomers. It is understood that all tautomers and mixtures of tautomers of the compounds of the present invention are included within the scope of the compounds of the present invention.

The present invention provides an IAP binding moiety together with a linker. A linker is a chemical linker group.

In one aspect the linker group is 4-20 atoms in shortest length. In one aspect the linker is a group comprising a length of 4-16 atoms in shortest length In one aspect the linker group Is a straight chain alkylene group of 4-20 carbon atoms in which one or more carbon atoms is replaced by a group independently selected from —O—, —NH—, —N(CH$_3$)—, —CO—, piperidine, piperazine, pyrimidinr, pyridine.

In one aspect the linker is a group comprising a length of 4-16 atoms in shortest length and hls a straight chain alkylene group of 4-20 carbon atoms in which one or more carbon atoms is replaced by a group independently selected from —O—, —NH—, —N(CH$_3$)—, —CO—, piperidine, piperazine, pyrimidinr, pyridine.

In a further aspect the linker group is a straight chain alkylene group of 4-16 carbon atoms wherein one or more carbon atoms are replaced by a group each independently selected from

—O—, —NH—, —N(CH$_3$)—,

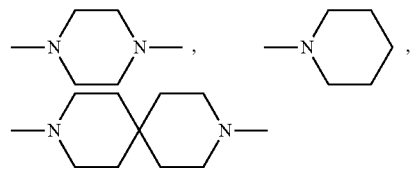

In further aspect of the invention there is provided an IAP binding moiety together with a linker which is a compound of Formula (II), (III), and (IV):

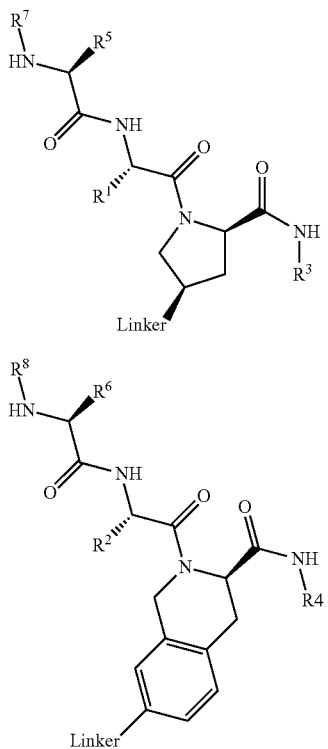

(II)

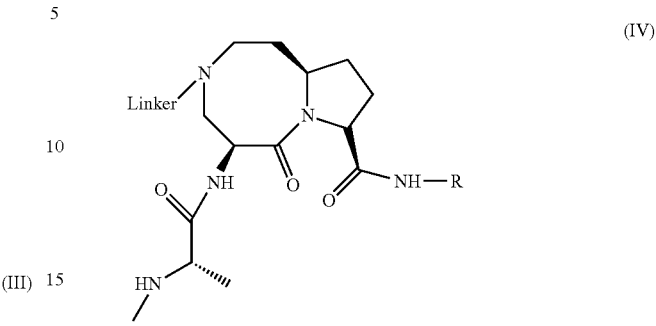

(IV)

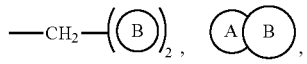

(III)

wherein

The linker is group comprising a length of 4-16 atoms in shortest length, $R^1$ and $R^2$ are independently optionally substituted alkyl, optionally substituted cycloalkyl, optionally substituted cycloalkylalkyl, optionally substituted arylalkyl, optionally substituted aryl, or $R^1$ and $R^2$ are independently optionally substituted thioalkyl wherein the substituents attached to the S atom of the thioalkyl are optionally substituted alkyl, optionally substituted branched alkyl, optionally substituted heterocyclyl, —(CH2)vCOR$_{20}$, —CH2CHR$_{21}$COR$_{22}$ or —CH$_2$R$_{23}$.

Wherein v-1-3, $R_{20}$ and $R_{22}$ are independently selected from OH, NR$_{24}$R$_{25}$ or OR$_{26}$, $R_{21}$ is NR$_{24}$R$_{25}$, R23 is optionally substituted aryl or optionally substituted heterocyclyl, where the optional substituents include alkyl and halogen, $R_{24}$ is hydrogen or optionally substituted alkyl, $R_{25}$ is hydrogen, optionally substituted alkyl, optionally substituted branched alkyl, optionally substituted arylalkyl, optionally substituted heterocyclyl, —CH2(OCH$_2$CH$_2$O)$_m$CH$_3$, or a polyamine chain, $R_{26}$ is optionally substituted alkyl, w=1-8, Where the optional substituents are OH, halogen or NH$_2$;

$R^3$ and $R^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted hetercycloalkyl, wherein the substitutents are alkyl, halogen or OH;

$R_5$, $R^6$, $R^7$ and $R^8$ are independently hydrogen, optionally substituted alkyl or optionally substituted cycloalkyl;

$R^9$ is hydrogen, optionally substituted alkyl, optionally substituted cycloalkyl or CO alkyl;

or a pharmaceutically acceptable salt thereof

Wherein the linker is a group comprising a length of 8-16 atoms in shortest length, R is selected from the group consisting of

wherein ring A is C$_{4-8}$ aliphatic ring,

—C$_{3-6}$cycloalkylene—(B), and —(CH2)$_{1-4}$—(B), wherein the B ring is aryl or nitrogen atom-containing heteroaryl and the B rings are optionally substituted;

or a pharmaceutically acceptable salt thereof.

In one aspect ring B is phenyl, napthyl, pyridinyl, pyrazinyl or pyrimidinyl.

In a further aspect of the invention there is provided a Protac compound comprising the compound of Formula (I), (II), (III) or (IV) linked via the linker to a compound which binds to a target protein, where said target protein is selected from the group consisting of structural proteins, receptors, enzymes, cell surface proteins, proteins pertinent to the integrated function of a cell, including proteins involved in catalytic activity, aromatase activity, motor activity, helicase activity, metabolic processes (anabolism and catabolism), antioxidant activity, proteolysis, biosynthesis, proteins with kinase activity, oxidoreductase activity, transferase activity, hydrolase activity, lyase activity, isomerise activity, ligase activity, enzyme regulator activity, signal transducer activity, structural molecule activity, binding activity (protein, lipid carbohydrate), receptor activity, cell motility, membrane fusion, cell communication, regulation of biological processes, development, cell differentiation, response to stimulus, behavioural proteins, cell adhesion proteins, proteins involved in cell death, proteins involved in transport (including protein transporter activity, nuclear transport, ion transporter activity, channel transporter activity, carrier activity, permease activity, secretion activity, electron transport activity, pathogenesis, chaperone regulator activity, nucleic acid binding activity, transcription regulator activity, extracellular organization and biogenesis activity and translation regulator activity.

In one embodiment there is a Protac which targets RIP 2 Kinase

The present invention also provides Protac compounds which modulate RIP2 kinase activity including degradation thereof have the following structure:

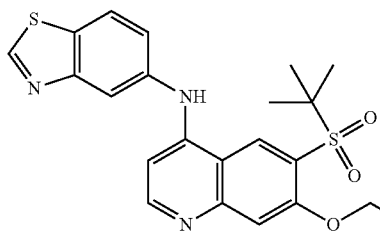
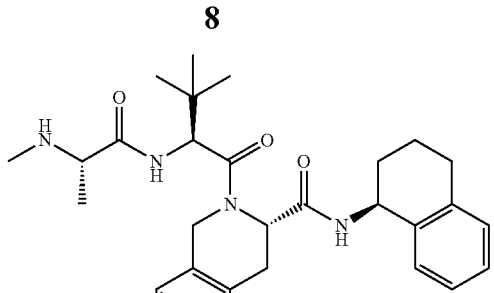
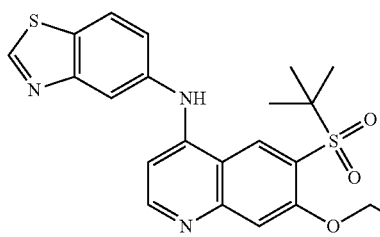
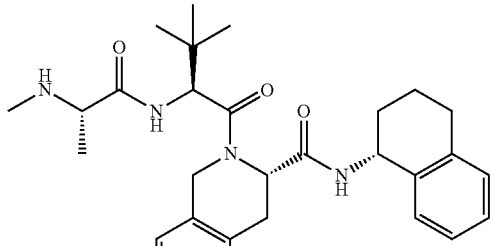

In one embodiment there is a Protac which targets the estrogen receptor

The present invention also provides Protac compounds which modulate estrogen receptor activity including degradation thereof including the following structure:

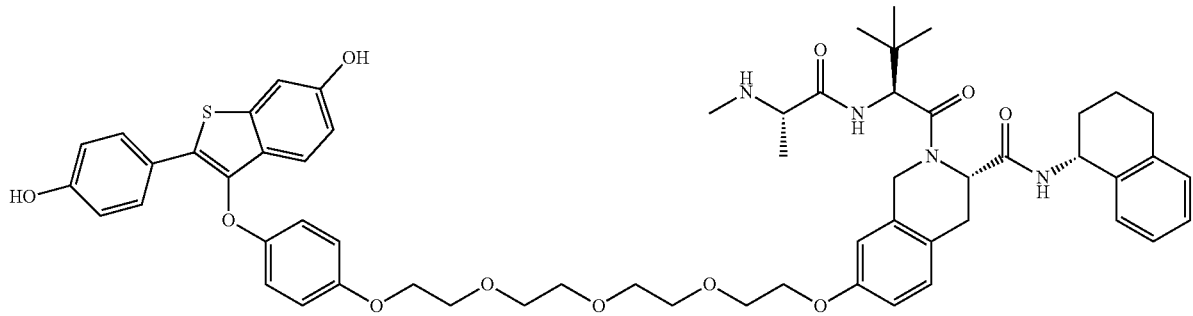 [SMILES: CN[C@@H](C)C(=O)N[C@H](C(=O)N1Cc2cc(OCCOCCOCCOCCOc3ccc(Oc4c(-c5ccc(O)cc5)sc5cc(O)ccc45)cc3)ccc2C[C@H]1C(=O)N[C@@H]1CCCc2ccccc21)C(C)(C)C]

In one embodiment there is a Protac which targets Bruton's tyrosine kinase (BTK)

The present invention also provides Protac compounds which modulate BTK activity including degradation thereof including the following structure:

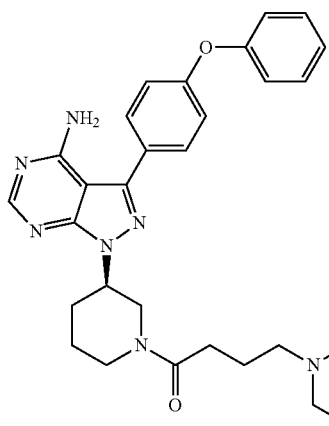
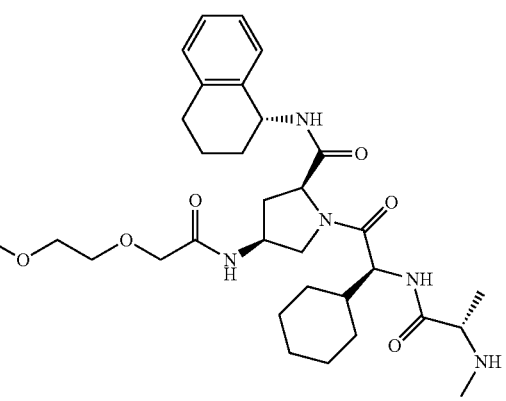

The compounds of Formula (I) may be in the form of a salt.

Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

Suitable pharmaceutically acceptable salts can include acid addition salts.

A pharmaceutically acceptable acid addition salt can be formed by reaction of a compound of formula (I) with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, p-toluenesulfonate, benzenesulfonate, methanesulfonate, ethanesulfonate, naphthalenesulfonate (e.g. 2-naphthalenesulfonate) salt.

Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of formula (I).

While it is possible that, for use in therapy, the compound of the invention may be administered as the raw chemical, it is possible to present the compound of the invention as the active ingredient as a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavouring, preservative, dispersing and colouring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like. The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories, rectal foams, rectal gels or as enemas.

Dosage forms for nasal or inhaled administration may conveniently be formulated as aerosols, solutions, suspensions drops, gels or dry powders.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In one aspect the pharmaceutical composition is suitable for oral or rectal administration for non systemic or local delivery to the GI tract, or is formulated for subcutaneous delivery.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions.

The amounts of the compound(s) of formula (I) or pharmaceutically acceptable salt(s) thereof and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

We have found that the IAP containing Protac compounds of the present invention, or a pharmaceutically acceptable salt thereof, or pharmaceutical compositions containing them, are capable of degrading the target protein.

Accordingly, the compounds of the present invention are expected to be potentially useful agents in the treatment of diseases or medical conditions mediated alone or in part by the target protein.

Provided herein are methods of treatment or prevention of diseases, disorders and conditions mediated by the target protein. A method may comprise administering to a subject, e.g. a subject in need thereof, a therapeutically effective amount of a compound of the invention.

Thus in one aspect there is provided a compound of the invention for use in therapy Thus in one aspect there is provided a compound of the invention for use in treating diseases, disorders or conditions mediated by the target protein Thus in one aspect there is provided the use of a compound of the invention in the manufacture of a medicament for treating diseases, disorders or conditions mediated by the target protein In a further aspect there is provided a method of treatment of diseases, disorders or conditions mediated by the target protein in a mammal comprising administering a therapeutically effective amount of a compound of the invention.

Diseases, disorders or conditions mediated by the target protein as used herein, denotes a condition or disorder which can be treated by modulating the function or activity of a target protein in a subject, wherein treatment comprises prevention, partial alleviation or cure of the condition or disorder. Modulation may occur locally, for example, within certain tissues of the subject, or more extensively throughout a subject being treated for such a condition or disorder.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order, by any convenient route in separate or combined pharmaceutical compositions.

The amounts of the compound(s) of formula (I) or pharmaceutically acceptable salt(s) thereof and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited. For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

The compounds of the invention may be particularly useful for treatment of RIP2 kinase-mediated diseases or disorders, particularly inflammatory disorders.

In one aspect the disease or condition is inflammation.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The compound of formula (I) may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of formula (I) include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of formula (I) include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of formula (I) include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of formula (I) include arthrosclerosis, arthritis, phlebitis, vasculitis, and lymphangitis.

Examples of inflammatory conditions of the digestive system which may be treated with the compounds of formula (I) include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of formula (I) include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compound of formula (I) may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compound of formula (I) may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic obstructive pulmonary disease, and inflammation accompanying infectious conditions (e.g., sepsis).

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, with or include one or more other therapeutic agents, for example selected from NSAIDS, corticosteroids, COX-2 inhibitors, cytokine inhibitors, anti-TNF agents, inhibitors oncostatin M, anti-malarials, immunsuppressive and cytostatics.

The compounds of the invention wherein the target protein is RIP2 kinase may be particularly useful for treatment of RIP2 kinase-mediated diseases or disorders, particularly, uveitis, interleukin-1 converting enzyme (ICE, also known as Caspase-1) associated fever syndrome, dermatitis, acute lung injury, type 2 diabetes mellitus, arthritis (specifically rheumatoid arthritis), inflammatory bowel disorders (such as ulcerative colitis and Crohn's disease), early-onset and extra-intestinal inflammatory bowel disease, prevention of ischemia reperfusion injury in solid organs (specifically kidney) in response ischemia induced by cardiac surgery, organ transplant, sepsis and other insults, liver diseases (non-alcohol steatohepatitis, alcohol steatohepatitis, and autoimmune hepatitis), allergic diseases (such as asthma), transplant reactions (such as graft versus host disease), autoimmune diseases (such as systemic lupus erythematosus, and multiple sclerosis), and granulomateous disorders (such as sarcoidosis, Blau syndrome, early-onset sarcoidosis, Wegner's granulomatosis, and interstitial pulmonary disease).

These compounds may be particularly useful in the treatment of uveitis, ICE fever, Blau Syndrome, early-onset sarcoidosis, ulcerative colitis, Crohn's disease, Wegener's granulamatosis and sarcoidosis.

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, particularly for the treatment of refractory cases, such as in combination with other anti-inflammatory and/or anti-TNF agents, which may be administered in therapeutically effective amounts as is known in the art.

For example, the compounds of this invention may be administered in combination with corticosteroids and/or anti-TNF agents to treat Blau syndrome, early-onset sarcoidosis; or in combination with anti-TNF biologics or other anti-inflammatory biologics to treat Crohn's Disease; or in combination with 5-ASA (mesalamine) or sulfasalazine to treat ulcerative colitis; or in combination with low-dose corticosteroids and/or methotrexate to treat Wegener's granulamatosis or sarcoidosis or interstitial pulmonary disease; or in combination with a biologic (e.g. anti-TNF, anti-IL-6, etc.) to treat rheumatoid arthritis; or in combination with anti-IL6 and/or methotrexate to treat ICE fever.

Examples of suitable anti-inflammatory agents include corticosteroids, particularly low-dose corticosteroids (such as prednisone) and anti-inflammatory biologics (such as anti-IL6R mAb and anti-CD20 mAb. Examples of suitable anti-TNF agents include anti-TNF biologics etanecerpt adalimumab), infliximab) and golimumab.

In one aspect the target protein is the estrogen receptor, BTK or other targets associated with cancer.

Examples of cancer diseases and conditions in which compounds of formula (I), or pharmaceutically acceptable salts or solvates thereof may have potentially beneficial antitumour effects include, but are not limited to, cancers of the lung, bone, pancreas, skin, head, neck, uterus, ovaries, stomach, colon, breast, esophagus, small intestine, bowel, endocrine system, thyroid glad, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. In one aspect the cancer is breast cancer.

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

In one embodiment, the compound of compound of formula (I) or a pharmaceutically acceptable salt thereof may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged.

In one embodiment, the further anti-cancer therapy is surgical and/or radiotherapy.

In one embodiment, the further anti-cancer therapy is at least one additional anti-neoplastic agent.

Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-Microtubule or Anti-Mitotic Agents:

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum Coordination Complexes:

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating Agents:

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic Anti-Neoplastics:

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II Inhibitors:

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite Neoplastic Agents:

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I Inhibitors:

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and Hormonal Analogues:

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, estrogens, and anti-estrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; antiestrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal Transduction Pathway Inhibitors:

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-Angiogenic Agents:

(i) Anti-angiogenic agents including non-receptor MEK angiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin $\alpha v \beta 3$ function, endostatin and angiostatin);

Immunotherapeutic Agents:

Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies Proapoptotic Agents:

Agents used in proapoptotic regimens (e.g., bcl-2 antisense oligonucleotides) may also be used in the combination of the present invention.

Cell Cycle Signalling Inhibitors

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In one embodiment, the combination of the present invention comprises a compound of formula I or a salt or solvate thereof and at least one anti-neoplastic agent which is an anti-microtubule agent selected from diterpenoids and vinca alkaloids.

In a further embodiment, at least one anti-neoplastic agent agent is a diterpenoid.

In a further embodiment, at least one anti-neoplastic agent is a vinca alkaloid.

In one embodiment, the combination of the present invention comprises a compound of formula I or a salt or solvate thereof and at least one anti-neoplastic agent, which is a platinum coordination complex.

In a further embodiment, at least one anti-neoplastic agent is paclitaxel, carboplatin, or vinorelbine.

In a further embodiment, at least one anti-neoplastic agent is carboplatin.

In a further embodiment, at least one anti-neoplastic agent is vinorelbine.

In a further embodiment, at least one anti-neoplastic agent is paclitaxel.

In one embodiment, the combination of the present invention comprises a compound of formula I and salts or solvates thereof and at least one anti-neoplastic agent which is a signal transduction pathway inhibitor.

In a further embodiment the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In a further embodiment the signal transduction pathway inhibitor is an inhibitor of a serine/threonine kinase rafk, akt, or PKC-zeta.

In a further embodiment the signal transduction pathway inhibitor is an inhibitor of a non-receptor tyrosine kinase selected from the src family of kinases.

In a further embodiment the signal transduction pathway inhibitor is an inhibitor of c-src.

In a further embodiment the signal transduction pathway inhibitor is an inhibitor of Ras oncogene selected from inhibitors of farnesyl transferase and geranylgeranyl transferase.

In a further embodiment the signal transduction pathway inhibitor is an inhibitor of a serine/threonine kinase selected from the group consisting of PI3K.

In a further embodiment the signal transduction pathway inhibitor is a dual EGFr/erbB2 inhibitor, for example N-{3-Chloro-4-[(3-fluorobenzyl)oxy]phenyl}-6-[5-({[2-(methanesulphonyl)ethyl]amino}methyl)-2-furyl]-4-quinazolinamine (structure below):

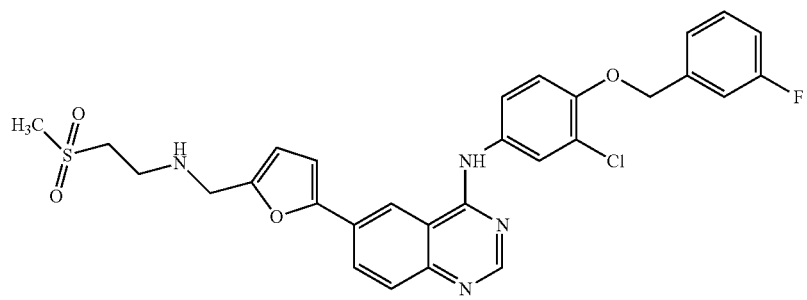 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present invention comprises a compound of formula I or a salt or solvate thereof and at least one anti-neoplastic agent which is a cell cycle signaling inhibitor.

In further embodiment, cell cycle signaling inhibitor is an inhibitor of CDK2, CDK4 or CDK6.

Particular components of combination therapy include combinations with other anti-estrogens including tamoxifen and/or fulvestrant.

In a further aspect there is provided a pharmaceutical composition comprising a combination comprising a compound of formula (I) or a pharmaceutically acceptable salt thereof and at least one further therapeutic agent useful in the treatment of a disease mediated by inhibition of the target protein and one or more of pharmaceutically acceptable excipients.

General Synthetic Methods

Compounds of general formula (I) may be prepared by methods known in the art of organic synthesis. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

In particular, methods for preparing IAP compounds included in the present invention can be found in WO 2014031487, WO 2014047024 WO 2008128171, WO2008/016893, WO 2014/060768, WO2014/060767, and WO15092420.

EXPERIMENTAL

Abbreviations

DCM: dichloromethane.
DIPEA: N,N-diisopropylethylamine.
DMF: N,N-dimethylformamide.
h: hour.
HATU: 2-(7-aza-1H-benzotriazole-1-yl)-1,1,3,3-tetramethyluronium hexafluorophosphate.
HPLC: high-performance liquid chromatography.
LCMS: liquid chromatography-mass spectrometry
Min: minutes.
NMR: Nuclear magnetic resonance.
RT: retention time.
tBu: tert-butyl.
TFA: trifluoroacetic acid.
THF: tetrahydrofuran.
LCMS Method A:
The analysis was conducted on an Acquity UPLC BEH C18 column (50 mm×2.1 mm internal diameter 1.7 μm packing diameter) at 40° C.
The solvents employed were:
A=0.1% v/v solution of formic acid in water.
B=0.1% v/v solution of formic acid in acetonitrile.
The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

LCMS Method B:
The analysis was conducted on an Acquity UPLC BEH C18 column (50 mm×2.1 mm internal diameter 1.7 μm packing diameter) at 40° C.
The solvents employed were:
A=10 mM ammonium bicarbonate in water adjusted to pH 10 with ammonia solution.
B=acetonitrile.
The gradient employed was as follows:

| Time (minutes) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was an averaged signal from wavelength of 210 nm to 350 nm and mass spectra were recorded on a mass spectrometer using alternate-scan positive and negative mode electrospray ionization.

The following illustrates the mobile phases and gradients used when compounds underwent purification by mass-directed autopreparative HPLC.

Mass-Directed Autooreoarative HPLC (Formic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of formic acid in water.
B=0.1% v/v solution of formic acid in acetonitrile.

Mass-Directed Autooreoarative HPLC (Trifluoroacetic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of trifluoroacetic acid in water.
B=0.1% v/v solution of trifluoroacetic acid in acetonitrile.

Mass-Directed Autooreoarative HPLC (Ammonium Bicarbonate Modifier)
The HPLC analysis was conducted on an XBridge C18 column (150 mm×30 mm internal diameter, 5 μm packing diameter) at ambient temperature.
The solvents employed were:
A=10 mM ammonium bicarbonate in water adjusted to pH 10 with ammonia solution.
B=acetonitrile.

For each of the mass-directed autopreparative purifications, irrespective of the modifier used, the gradient employed was dependent upon the retention time of the particular compound undergoing purification as recorded in the analytical LCMS, and was as follows:

For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ChemBioDraw Ultra v12 from CambridgeSoft.

(S)-Tert-butyl 7-hydroxy-3-(((R)-1,2,3,4-tetrahydronaphthalen-1-yl)carbamoyl)-3,4-dihydroisoquinoline-2(1H)-carboxylate

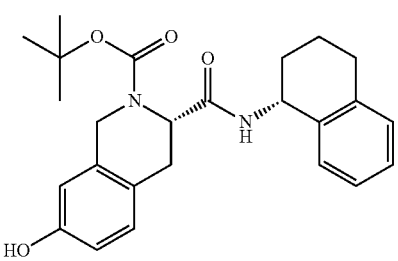 [SMILES: CC(C)(C)OC(=O)N1Cc2cc(O)ccc2C[C@H]1C(=O)N[C@@H]1CCCc2ccccc21]

A mixture of (S)-2-(tert-butoxycarbonyl)-7-hydroxy-1,2,3,4-tetrahydroisoquinoline-3-carboxylic acid (commercially available from, for example, Fluorochem) (1 g, 3.41 mmol) and (R)-1,2,3,4-tetrahydronaphthalen-1-amine (commercially available from, for example, Aldrich) (0.552 g, 3.75 mmol) in DMF (4 mL) was treated with DIPEA (1.79 mL, 10.2 mmol) and then with HATU (1.56 g, 4.09 mmol) and stirred at ambient temperature for 30 minutes. The mixture was treated with dichloromethane (60 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (1.18 g, 2.79 mmol, 82% yield). LCMS RT=1.10 min, ES+ve 423.

(S)-7-Hydroxy-N—((R)-1,2,3,4-tetrahydronaphtalen-1-yl)-1,2,3,4-tetrahydroisoquinoline-3-carboxamide, Hydrochloride

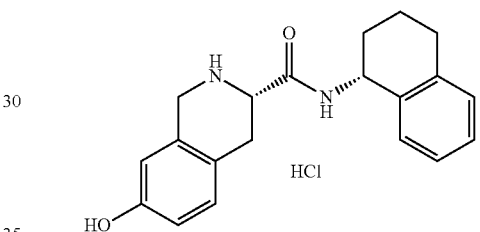

A solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.18 g, 2.79 mmol) in tetrahydrofuran (10 mL) was treated with hydrochloric acid (4M in 1,4-dioxan) (10 mL, 40 mmol) and the mixture was stood at ambient temperature overnight. The mixture was removed of solvent in vacuo to afford the title compound (943 mg, 2.63 mmol, 94% yield). LCMS RT=0.58 min, ES+ve 323.

Tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate

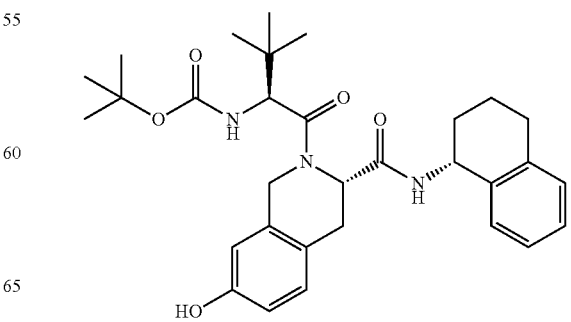

A mixture of (S)-7-hydroxy-N—((R)-1,2,3,4-tetrahydronaphthalen-1-yl)-1,2,3,4-tetrahydroisoquinoline-3-carboxamide, Hydrochloride (933 mg, 2.60 mmol) and (S)-2-((tert-butoxycarbonyl)amino)-3,3-dimethylbutanoic acid (631 mg, 2.73 mmol) in DMF (10 mL) was treated with DIPEA (1.82 mL, 10.4 mmol) and then with HATU (1.19 g, 3.12 mmol) and stirred at ambient temperature for 1 hour. The mixture was treated with dichloromethane (80 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (923 mg, 1.72 mmol, 66% yield). LCMS RT=1.27 min, ES+ve 536.

(S)-2-((S)-2-Amino-3,3-dimethylbutanoyl)-7-hydroxy-N—((R)-1,2,3,4-tetrahydronaphthalen-1-yl)-1,2,3,4-tetrahydroisoquinoline-3-carboxamide, Hydrochloride

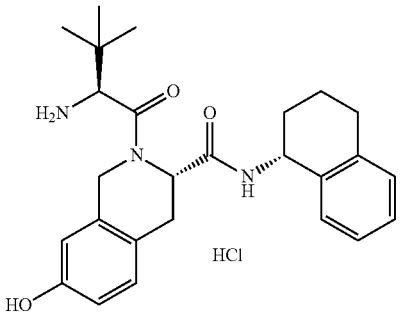 [SMILES: CC(C)(C)[C@H](N)C(=O)N1Cc2cc(O)ccc2C[C@H]1C(=O)N[C@@H]1CCCc2ccccc21 ; Cl]

A solution of tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate (915 mg, 1.71 mmol) in tetrahydrofuran (4 mL) was treated with hydrochloric acid (4M in 1,4-dioxan) (5 mL, 165 mmol) and then stirred at ambient temperature overnight. The mixture was evaporated to dryness to afford the title compound (780 mg, 1.65 mmol, 97% yield). LCMS RT=0.69 min, ES+ve 436.

Tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

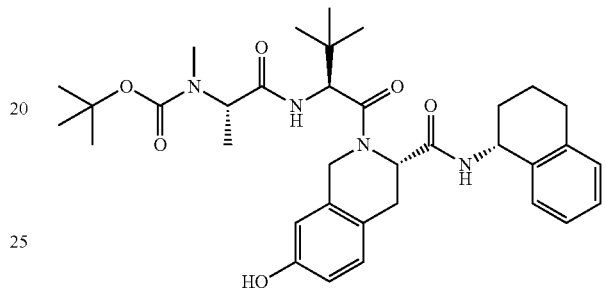

A mixture of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide, Hydrochloride (770 mg, 1.63 mmol) and (S)-2-((tert-butoxycarbonyl)(methyl)amino)propanoic acid (332 mg, 1.63 mmol) in DMF (4 mL) was treated with DIPEA (1.14 mL, 6.53 mmol) and then with HATU (744 mg, 1.96 mmol) and stirred at ambient temperature overnight. The product was purified by chromatography on silica using a gradient elution from 0% to 100% ethyl acetate in cyclohexane to afford the title compound (780 mg, 1.26 mmol, 77% yield). LCMS RT=1.29 min, ES+ve 621.

Tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

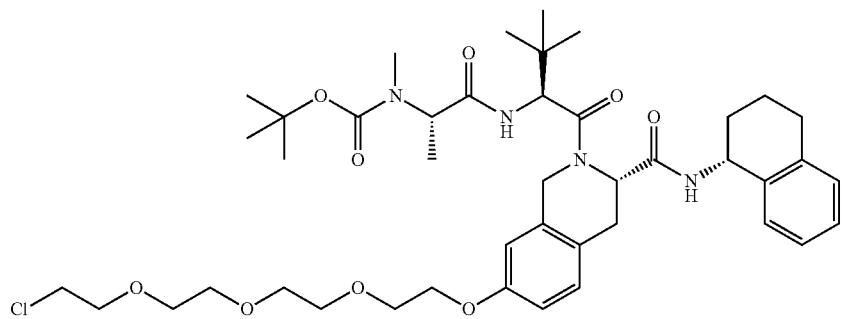 [SMILES: C[C@@H](C(=O)N[C@H](C(=O)N1Cc2cc(OCCOCCOCCOCCCl)ccc2C[C@H]1C(=O)N[C@@H]1CCCc2ccccc21)C(C)(C)C)N(C)C(=O)OC(C)(C)C]

A solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (200 mg, 0.322 mmol) in DMF (4 mL) was treated with 1-chloro-2-(2-(2-(2-chloroethoxy)ethoxy)ethoxy)ethane (commercially available from, for example, Aldrich) (298 mg, 1.29 mmol) and potassium carbonate (134 mg, 0.97 mmol) and heated at 80° C. overnight. The product was subjected directly to purification by mass-directed automated preparative HPLC (formic acid modifier) to afford the title compound (165 mg, 0.202 mmol, 62.8% yield). LCMS RT=1.44 min, ES+ve 816.

5-(((4-Bromo-3-methoxyphenyl)amino)methylene)-2,2-dimethyl-1,3-dioxane-4,6-dione

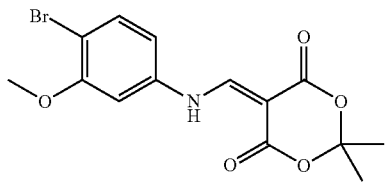

2,2-Dimethyl-1,3-dioxane-4,6-dione (8.5 g, 58 mmol) in trimethyl orthoformate (50 mL, 450 mmol) was refluxed at 105° C. for 1 hr. 4-Bromo-3-methoxyaniline (commercially available from, for example, Aldrich) (10.5 g, 50.4 mmol) was then added and refluxing was continued for an additional hour. The suspension was filtered, and the solid was washed with methanol and vacuum dried to yield the title compound (17.0 g, 49 mmol, 96% yield). LCMS RT=1.10 min, ES+ve 356,358

6-Bromo-7-methomiquinolin-4-ol

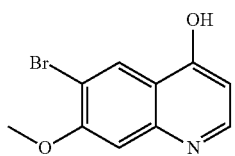

To diphenyl ether (68 mL, 420 mmol) at 230° C. was added 5-({[4-bromo-3-(methyloxy)phenyl]amino}methylidene)-2,2-dimethyl-1,3-dioxane-4,6-dione (15 g, 42 mmol), and the mixture was stirred for 1 hr. The reaction mixture was poured into hexane after being cooled to room temperature. The precipitate was filtered and washed with hexane. The brown solid was dried under vacuum overnight to afford the title compound (10.0 g, 33 mmol, 79% yield). LCMS RT=0.63 min, ES+ve 254,256

6-Bromo-4-chloro-7-methoxyquinoline

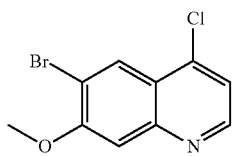

6-Bromo-7-(methyloxy)-4-quinolinol (4.17 g, 16.4 mmol) in phosphorus oxychloride (8 mL, 82 mmol) was stirred at 110° C. for 1 hr. The reaction mixture was cooled and cautiously poured into saturated aqueous sodium carbonate with ice while stirring. The resulting suspension was filtered, the solid was washed with water and vacuum-dried overnight to yield the title compound (4.6 g, 16 mmol, 97% yield). LCMS RT=1.18 min, ES+ve 272,274

6-(Tert-butylthio)-4-chloro-7-methoxyquinoline

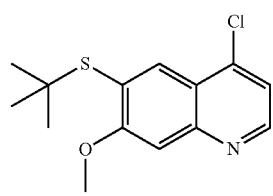 [SMILES: COc1cc2nccc(Cl)c2cc1SC(C)(C)C]

A mixture of 6-bromo-4-chloro-7-methoxyquinoline (50 g, 183 mmol), Pd(PPh$_3$)$_4$ (5.30 g, 4.59 mmol), sodium carbonate (48.6 g, 459 mmol) and 1,4-dioxane (895 mL) was purged with nitrogen for 10 minutes. 2-Methyl-2-propanethiol (22.8 mL, 202 mmol) was added and the reaction was heated at 70° C. for 4 days. The reaction was cooled to rt and flushed through a silica gel plug that had been pre-wetted with EtOAc using 100% EtOAc as the eluent. The product-containing fractions were combined and triturated with MeOH to afford the title compound (37.5 g, 128 mmol, 70% yield). LCMS RT=1.31 min, ES+ve 282

6-(Tert-butylsulfonyl)-4-chloro-7-methoxyquinoline

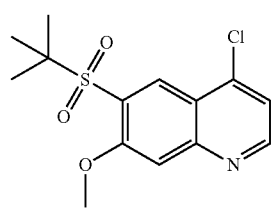 [SMILES: COc1cc2nccc(Cl)c2cc1S(=O)(=O)C(C)(C)C]

(Tert-butylthio)-4-chloro-7-methoxyquinoline (18.5 g, 63.0 mmol) in ethyl acetate (315 mL) and water (315 mL) was treated with Oxone® (44.6 g, 72.5 mmol) and stirred at rt for 18 hours. The mixture was separated and the aqueous phase was extracted twice with ethyl acetate. The combined organic extracts were concentrated to dryness. The residue was dissolved in a minimal amount of 10% methanol/dichloromethane, loaded onto a 340 g pre-packed silica cartridge and purified via column chromatography (100% ethyl acetate, then 0-20% methanol in ethyl acetate). Product-containing fractions were evaporated to dryness and triturated with EtOAc to yield the title compound (15.2 g, 48.4 mmol, 77% yield). LCMS RT=0.97 min, ES+ve 314

N-(6-(Tert-butylsulfonyl)-7-methoxyquinolin-4-yl)benzo[d]thiazol-5-amine

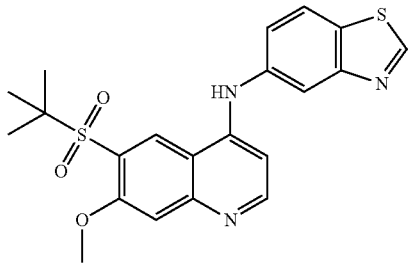 [SMILES: COc1cc2nccc(Nc3ccc4scnc4c3)c2cc1S(=O)(=O)C(C)(C)C]

A mixture of 6-(tert-butylsulfonyl)-4-chloro-7-methoxyquinoline (2 g, 6.37 mmol) and benzo[d]thiazol-5-amine (0.957 g, 6.37 mmol) in ethanol (10 mL) was irradiated by microwave at 150° C. for 15 mins. The reaction mixture was partitioned between ethyl acetate and saturated sodium bicarbonate. The aqueous layer was extracted with EtOAc twice and the combined EtOAc layers were dried over magnesium sulfate, filtered and evaporated to dryness. The residue was purified via flash chromatography (100 g prepacked silica cartridge, 0-75% ethyl acetate/cyclohexane) to yield the title compound (2.11 g, 4.94 mmol, 77% yield). LCMS RT=0.58 min, ES+ve 428

4-(Benzo[d]thiazol-5-ylamino)-6-(tert-butylsulfonyl)quinolin-7-ol

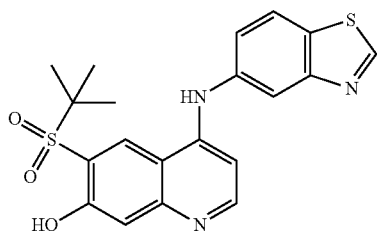 [SMILES: CC(C)(C)S(=O)(=O)c1cc2c(Nc3ccc4scnc4c3)ccnc2cc1O]

To a solution of N-(6-(tert-butylsulfonyl)-7-methoxyquinolin-4-yl)benzo[d]thiazol-5-amine hydrochloride (5.35 g, 11.53 mmol) in DMF (50 mL) was added sodium propane-2-thiolate (5.66 g, 57.7 mmol). The reaction was then heated to 150° C. for 1 hour. It was cooled to rt and concentrated under vacuum. The residue was treated with ethanol (70 mL) and stirred at 60° C. for 15 minutes, cooled in ice then the yellow precipitated product was filtered off, washed with minimum ethanol and dried under vacuum to afford the title compound (4.55 g, 11mmol, 95% yield). LCMS RT=0.57 min, ES+ve 414

(S)-Tert-butyl 7-hydroxy-3-(((R)-1,2,3,4-tetrahydronaphthalen-1-yl)carbamoyl)-3,4-dihydroisoquinoline-2(1H)-carboxylate A mixture of (S)-2-(tert-butoxycarbonyl)-7-hydroxy-1,2,3,4-tetrahydroisoquinoline-3-carboxylic acid (commercially available from, for example, Fluorochem) (1 g, 3.41 mmol) and (R)-1,2,3,4-tetrahydronaphthalen-1-amine (commercially available from, for example, Aldrich) (0.552 g, 3.75 mmol) in DMF (4 mL) was treated with DIPEA (1.79 mL, 10.2 mmol) and then with HATU (1.56 g, 4.09 mmol) and stirred at ambient temperature for 30 minutes. The mixture was treated with dichloromethane (60 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (1.18 g, 2.79 mmol, 82% yield). LCMS RT=1.10 min, ES+ve 423.

(S)-7-Hydroxy-N—((R)-1,2,3,4-tetrahydronaphthalen-1-yl)-1,2,3,4-tetrahydroisoquinoline-3-carboxamide, Hydrochloride A solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.18 g, 2.79 mmol) in tetrahydrofuran (10 mL) was treated with hydrochloric acid (4M in 1,4-dioxan) (10 mL, 40 mmol) and the mixture was stood at ambient temperature overnight. The mixture was removed of solvent in vacuo to afford the title compound (943 mg, 2.63 mmol, 94% yield). LCMS RT=0.58 min, ES+ve 323.

Tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate

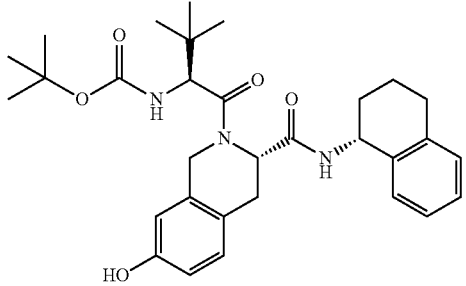 [SMILES: CC(C)(C)OC(=O)N[C@H](C(=O)N1Cc2cc(O)ccc2C[C@H]1C(=O)N[C@@H]1CCCc2ccccc21)C(C)(C)C]

A mixture of (S)-7-hydroxy-N—((R)-1,2,3,4-tetrahydronaphthalen-1-yl)-1,2,3,4-tetrahydroisoquinoline-3-carboxamide, Hydrochloride (933 mg, 2.60 mmol) and (S)-2-((tert-butoxycarbonyl)amino)-3,3-dimethylbutanoic acid (631 mg, 2.73 mmol) in DMF (10 mL) was treated with DIPEA (1.82 mL, 10.4 mmol) and then with HATU (1.19 g, 3.12 mmol) and stirred at ambient temperature for 1 hour. The mixture was treated with dichloromethane (80 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (923 mg, 1.72 mmol, 66% yield). LCMS RT=1.27 min, ES+ve 536.

(S)-2-((S)-2-Amino-3,3-dimethylbutanoyl)-7-hydroxy-N—((R)-1,2,3,4-tetrahydronaphthalen-1-yl)-1,2,3,4-tetrahydroisoquinoline-3-carboxamide, Hydrochloride

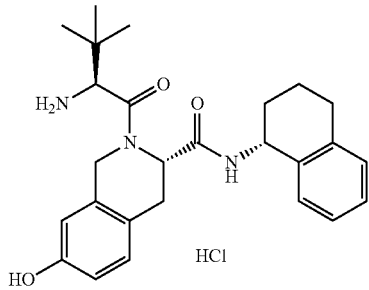 [SMILES: CC(C)(C)[C@H](N)C(=O)N1Cc2cc(O)ccc2C[C@H]1C(=O)N[C@@H]1CCCc2ccccc21 ; Cl]

A solution of tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate (915 mg, 1.71 mmol) in tetrahydrofuran (4 mL) was treated with hydrochloric acid (4M in 1,4-dioxan) (5 mL, 165 mmol) and then stirred at ambient temperature overnight. The mixture was evaporated to dryness to afford the title compound (780 mg, 1.65 mmol, 97% yield). LCMS RT=0.69 min, ES+ve 436.

Tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

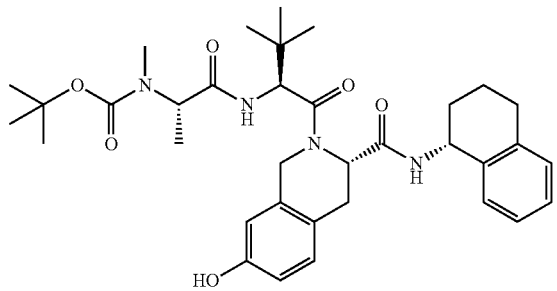 [SMILES: C[C@@H](C(=O)N[C@H](C(=O)N1Cc2cc(O)ccc2C[C@H]1C(=O)N[C@@H]1CCCc2ccccc21)C(C)(C)C)N(C)C(=O)OC(C)(C)C]

A mixture of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide, Hydrochloride (770 mg, 1.63 mmol) and (S)-2-((tert-butoxycarbonyl)(methyl)amino)propanoic acid (332 mg, 1.63 mmol) in DMF (4 mL) was treated with DIPEA (1.14 mL, 6.53 mmol) and then with HATU (744 mg, 1.96 mmol) and stirred at ambient temperature overnight. The product was purified by chromatography on silica using a gradient elution from 0% to 100% ethyl acetate in cyclohexane to afford the title compound (780 mg, 1.26 mmol, 77% yield). LCMS RT=1.29 min, ES+ve 621.

Tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

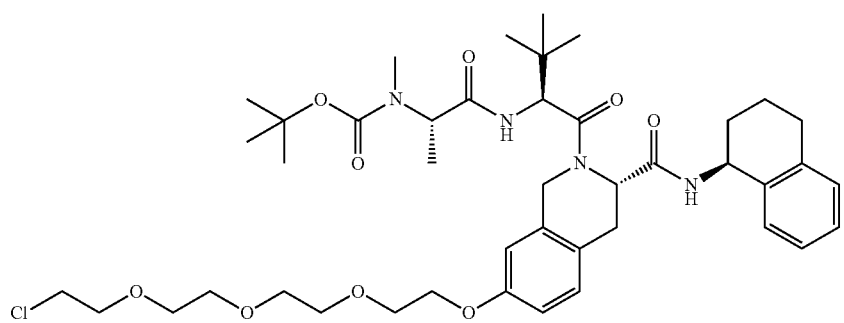 [SMILES: C[C@@H](C(=O)N[C@H](C(=O)N1Cc2cc(OCCOCCOCCOCCCl)ccc2C[C@H]1C(=O)N[C@H]1CCCc2ccccc21)C(C)(C)C)N(C)C(=O)OC(C)(C)C]

A solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (200 mg, 0.322 mmol) in DMF (4 mL) was treated with 1-chloro-2-(2-(2-(2-chloroethoxy)ethoxy)ethoxy)ethane (commercially available from, for example, Aldrich) (298 mg, 1.29 mmol) and potassium carbonate (134 mg, 0.97 mmol) and heated at 80° C. overnight. The product was subjected directly to purification by mass-directed automated preparative HPLC (formic acid modifier) to afford the title compound (165 mg, 0.202 mmol, 62.8% yield). LCMS RT=1.44 min, ES+ve 816.

Tert-butyl (((S)-1-(((S)-1-((S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate A mixture of (S)-2-(tert-butoxycarbonyl)-7-hydroxy-1,2,3,4-tetrahydroisoquinoline-3-carboxylic acid (commercially available from, for example, Fluorochem) (1 g, 3.41 mmol) and (R)-1,2,3,4-tetrahydronaphthalen-1-amine (commercially available from, for example, Aldrich) (0.552 g, 3.8 mmol) in DMF (4 mL) was treated with DIPEA (1.8 mL, 10.2 mmol) and then with HATU (1.56 g, 4.1 mmol) and stirred at ambient temperature for 30 minutes. The mixture was treated with dichloromethane (60 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (1.18 g, 2.8 mmol, 82% yield). LCMS RT=1.10 min, ES+ve 423.

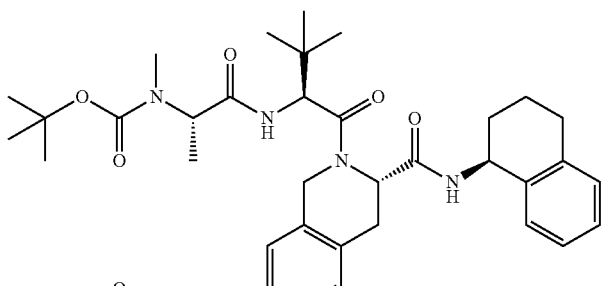

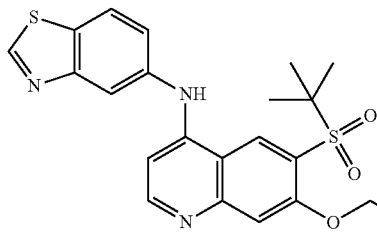

A mixture of 4-(benzo[d]thiazol-5-ylamino)-6-(tert-butylsulfonyl)quinolin-7-ol (61 mg, 0.147 mmol), tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (80 mg, 0.098 mmol) and potassium carbonate (41 mg, 0.29 mmol) in DMF (1.5 mL) was heated at 105° C. for 8 hours. The product was subjected directly to purification by mass-directed automated preparative HPLC (formic acid modifier) to afford the title compound (78 mg, 0.065 mmol, 67% yield). LCMS RT=1.11 min, ES+ve 1193.

(S)-Tert-butyl 7-hydroxy-3-(((R)-1,2,3,4-tetrahydronaphthalen-1-yl)carbamoyl)-3,4-dihydroisoquinoline-2(1H)-carboxylate

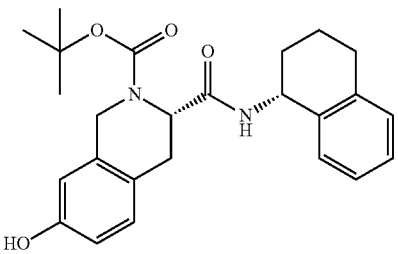 [SMILES: CC(C)(C)OC(=O)N1Cc2cc(O)ccc2C[C@H]1C(=O)N[C@@H]1CCCc2ccccc21]

(S)-7-Hydroxy-N—((R)-1,2,3,4-tetrahydronaphthalen-1-yl)-1,2,3,4-tetrahydroisoquinoline-3-carboxamide, Hydrochloride

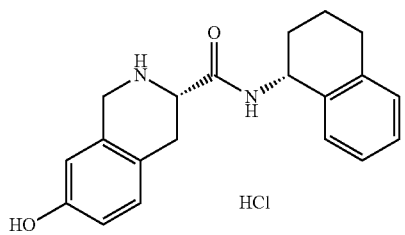 [SMILES: O=C(N[C@@H]1CCCc2ccccc21)[C@@H]1Cc2ccc(O)cc2CN1 ; Cl]

A solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.18 g, 2.8 mmol) in tetrahydrofuran (10 mL) was treated with hydrochloric acid (4M in 1,4-dioxan) (10 mL, 40 mmol) and the mixture was stood at ambient temperature overnight. The mixture was removed of solvent in vacuo to afford the title compound (943 mg, 2.6 mmol, 94% yield). LCMS RT=0.58 min, ES+ve 323.

Tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate

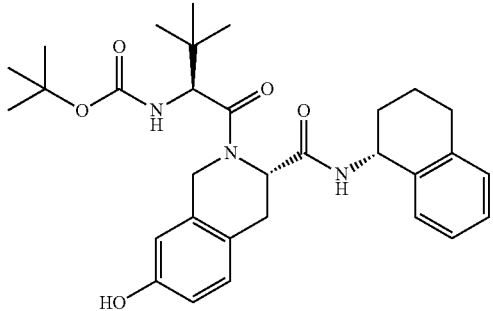 [SMILES: CC(C)(C)OC(=O)N[C@H](C(=O)N1Cc2cc(O)ccc2C[C@H]1C(=O)N[C@@H]1CCCc2ccccc21)C(C)(C)C]

A mixture of (S)-7-hydroxy-N—((R)-1,2,3,4-tetrahydronaphthalen-1-yl)-1,2,3,4-tetrahydroisoquinoline-3-carboxamide, hydrochloride (933 mg, 2.6 mmol) and (S)-2-((tert-butoxycarbonyl)amino)-3,3-dimethylbutanoic acid (631 mg, 2.7 mmol) in DMF (10 mL) was treated with DIPEA (1.82 mL, 10.4 mmol) and then with HATU (1.19 g, 3.12 mmol) and stirred at ambient temperature for 1 hour. The mixture was treated with dichloromethane (80 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (923 mg, 1.72 mmol, 66% yield). LCMS RT=1.27 min, ES+ve 536.

(S)-2-((S)-2-Amino-3,3-dimethylbutanoyl)-7-hydroxy-N—((R)-1,2,3,4-tetrahydronaphthalen-1-yl)-1,2,3,4-tetrahydroisoquinoline-3-carboxamide, Hydrochloride

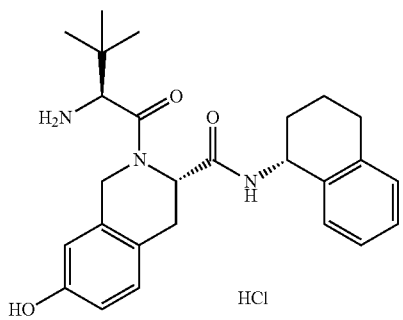 [SMILES: CC(C)(C)[C@H](N)C(=O)N1Cc2cc(O)ccc2C[C@H]1C(=O)N[C@@H]1CCCc2ccccc21 ; Cl]

A solution of tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate (915 mg, 1.71 mmol) in tetrahydrofuran (4 mL) was treated with hydrochloric acid (4M in 1,4-dioxan) (5 mL, 20 mmol) and then stirred at ambient temperature overnight. The mixture was evaporated to dryness to afford the title compound (780 mg, 1.65 mmol, 97% yield). LCMS RT=0.69 min, ES+ve 436.

Tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

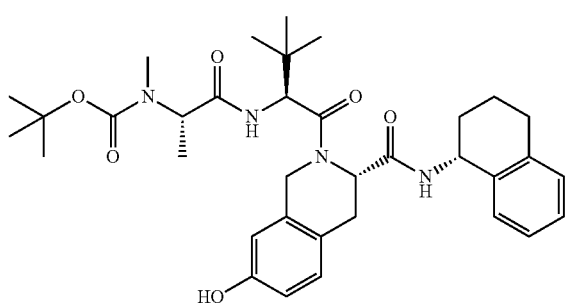 [SMILES: C[C@@H](C(=O)N[C@H](C(=O)N1Cc2cc(O)ccc2C[C@H]1C(=O)N[C@@H]1CCCc2ccccc21)C(C)(C)C)N(C)C(=O)OC(C)(C)C]

A mixture of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide, hydrochloride (770 mg, 1.63 mmol) and (S)-2-((tert-butoxycarbonyl)(methyl)amino)propanoic acid (332 mg, 1.63 mmol) in DMF (4 mL) was treated with DIPEA (1.14 mL, 6.5 mmol) and then with HATU (744 mg, 2.0 mmol) and stirred at ambient temperature overnight. The product was purified by chromatography on silica using a gradient elution from 0% to 100% ethyl acetate in cyclohexane to afford the title compound (780 mg, 1.26 mmol, 77% yield). LCMS RT=1.29 min, ES+ve 621.

Tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

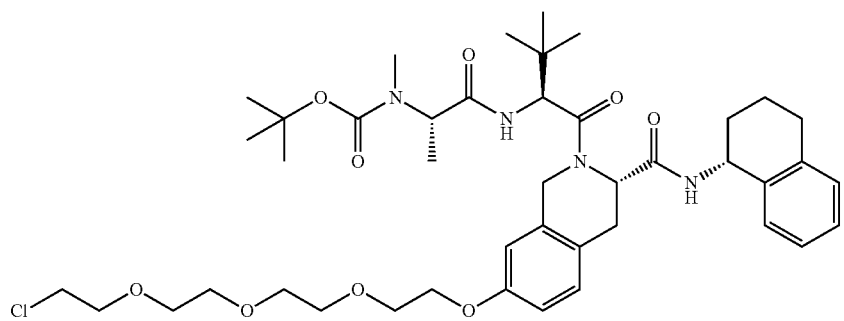 [SMILES: C[C@@H](C(=O)N[C@H](C(=O)N1Cc2cc(OCCOCCOCCOCCCl)ccc2C[C@H]1C(=O)N[C@@H]1CCCc2ccccc21)C(C)(C)C)N(C)C(=O)OC(C)(C)C]

A solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (200 mg, 0.32 mmol) in DMF (4 mL) was treated with 1-chloro-2-(2-(2-(2-chloroethoxy)ethoxy)ethoxy)ethane (commercially available from, for example, Aldrich) (298 mg, 1.3 mmol) and potassium carbonate (134 mg, 1.0 mmol) and heated at 80° C. overnight. The product was subjected directly to purification by mass-directed automated preparative HPLC (formic acid modifier) to afford the title compound (165 mg, 0.20 mmol, 63% yield). LCMS RT=1.44 min, ES+ve 816.

Tert-butyl ((S)-1-(((S)-1-((S)-7-(2-(2-(2-(2-(4-((6-(benzyloxy)-2-(4-(benzyloxy)phenyl)benzo[b]thiophen-3-yl)oxy)phenoxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

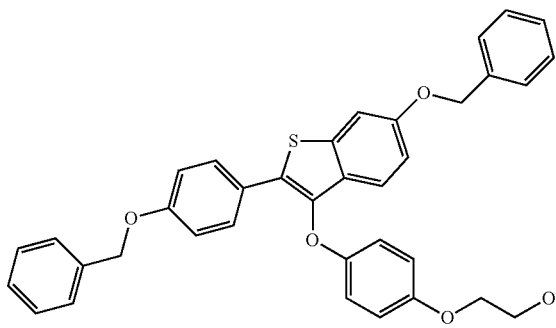
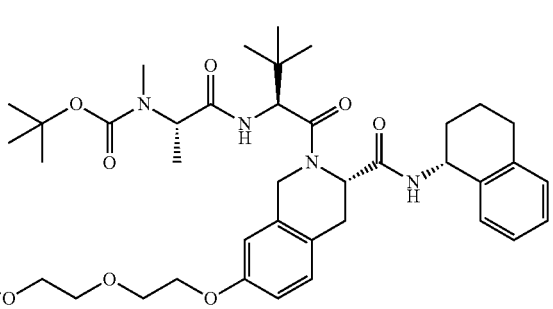

A mixture of 4-((6-(benzyloxy)-2-(4-(benzyloxy)phenyl)benzo[b]thiophen-3-yl)oxy)phenol (23 mg, 0.044 mmol, prepared as in patent WO 2015/000867), tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (30 mg, 0.037 mmol) and potassium carbonate (15 mg, 0.11 mmol) in DMF (1.5 mL) was heated at 105° C. for 6 hours. The product was subjected directly to purification by mass-directed automated preparative HPLC (formic acid modifier) to afford the title compound (31 mg, 0.024 mmol, 64% yield).

tert-Butyl ((S)-1-(((S)-2-((2S,4S)-4-(14-chloro-3,6,9,12-tetraoxatetradecanamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate

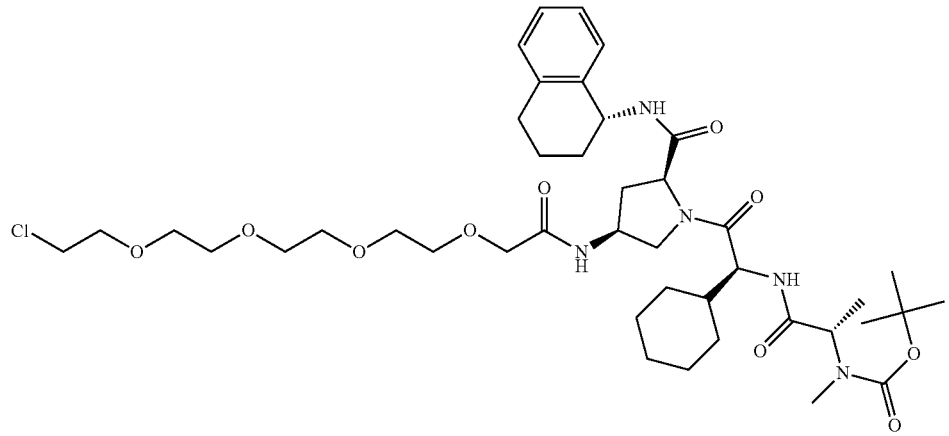 [SMILES: C[C@@H](C(=O)N[C@H](C(=O)N1C[C@@H](NC(=O)COCCOCCOCCOCCCl)C[C@H]1C(=O)N[C@@H]1CCCc2ccccc21)C1CCCCC1)N(C)C(=O)OC(C)(C)C]

To a stirred solution of 14-chloro-3,6,9,12-tetraoxatetradecan-1-oic acid (111 mg, 0.411 mmol) and HATU (169 mg, 0.445 mmol) in DMF (3 mL) was added DIPEA (0.180 mL, 1.03 mmol) and the mixture stirred at rt for 10 min. tert-Butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (200 mg, 0.343 mmol, prepared as described in WO2014090709) was then added and the mixture stirred at room temoerarture for 1 h. The reaction mixture was partially concentrated under a stream of nitrogen, then the mixture directly purified by MDAP (ammonium carbonate modifier gradient). The appropriate fractions were collected and acetonitrile removed in vacuo, then the aqueous layer extracted with DCM (50 mL). The organic extract was collected and evaporated in vacuo to give the title compound (224 mg) as a colourless gum. LCMS RT=1.36 min, ES−ve 834.5

(E)-4-(4-(14-(((3S,5S)-1-((S)-2-((S)-2-((tert-Butoxycarbonyl)(methyl)amino)propanamido)-2-cyclohexylacetyl)-5-(((R)-1,2,3,4-tetrahydronaphthalen-1-yl)carbamoyl)pyrrolidin-3-yl)amino)-14-oxo-3,6,9,12-tetraoxatetradecyl)piperazin-1-yl)but-2-enoic acid

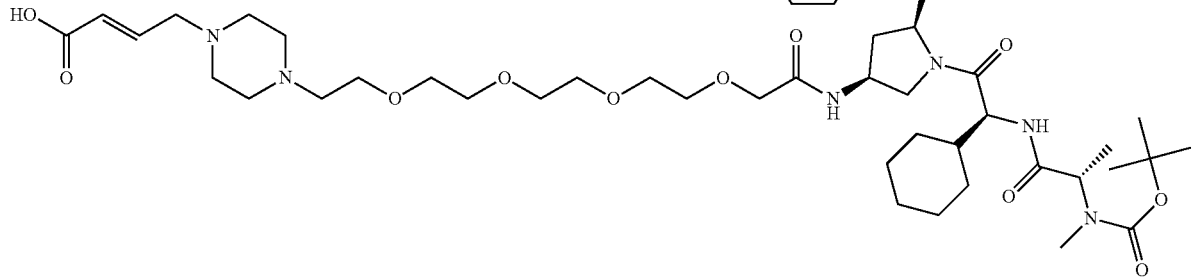

To a stirred solution of tert-butyl ((S)-1-(((S)-2-((2S,4S)-4-(14-chloro-3,6,9,12-tetraoxatetradecanamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (526 mg, 0.629 mmol) in acetonitrile (5 mL) was added piperazine (433 mg, 5.03 mmol) then the mixture heated at 150° C. in the microwave for 1 h. The solution was poured into a mixture of DCM (100 mL) and water (100 mL), the pH adjusted to 8 with HCl (2 M aq.), then the phases were separated. The aqueous layer was back-extracted with DCM (2×50 mL), then the organic layers were combined, dried using a hydrophobic frit and evaporated in vacuo.

The residue was directly dissolved in DMF (5 mL), then DIPEA (0.329 mL, 1.89 mmol) was added, followed by (E)-4-bromobut-2-enoic acid (125 mg, 0.755 mmol), then the mixture stirred at rt for 3 h. The reaction mixture was concentrated under a stream of nitrogen, then directly loaded onto reverse phase (C18) 60 g and purified using a 15-55% acetonitrile-water (ammonium carbonate modifier) gradient. The appropriate fractions were combined and evaporated in vacuo to give the title compound (351 mg) as a white solid. LCMS: RT=0.90 rains, ES+=970.8 tert-Butyl ((S)-1-(((S)-2-((2S,4S)-4-(14-(4-((E)-4-((R)-3-(4-amino-3-(4-phenoxyphenyl)-1H-pyrazolo[3,4-d]pyrimidin-1-yl)piperidin-1-yl)-4-oxobut-2-en-1-yl)piperazin-1-yl)-3,6,9,12-tetraoxatetradecanamido)-2-(((R)-1,2,3,4-tetrahydronapthalen-1-yl)carbamoyl)pyrrolidin-1-yl)-1-cyclohexyl-2-oxoethyl)amino)-1-oxopropan-2-yl)(methyl)carbamate

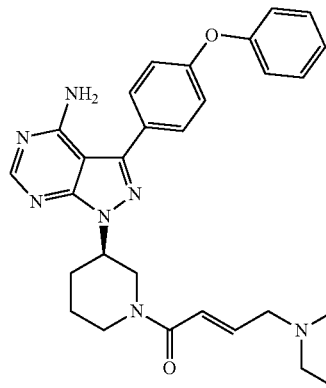
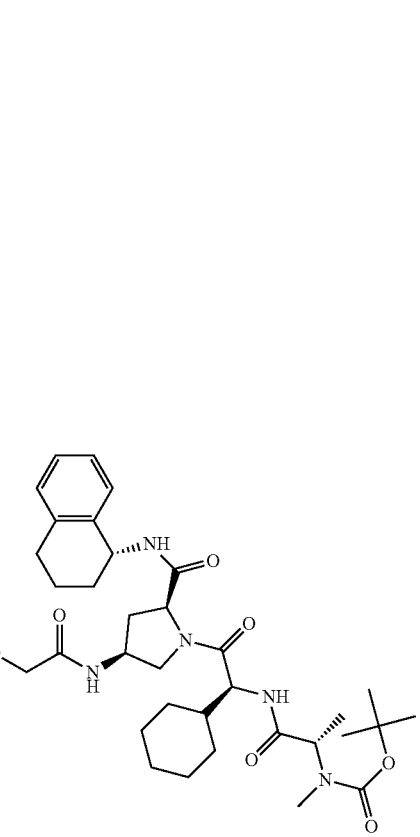

To a stirred solution of (E)-4-(4-(14-(((3S,5S)-1-((S)-2-((S)-2-((tert-butoxycarbonyl)methyl)amino) propanamido)-2-cyclohexylacetyl)-5-(((R)-1,2,3,4-tetrahydronaphthalen-1-yl)carbamoyl)pyrrolidin-3-yl)amino)-14-oxo-3,6,9,12-tetraoxatetradecyl)piperazin-1-yl)but-2-enoic acid (148 mg, 0.153 mmol), (R)-3-(4-phenoxyphenyl)-1-(piperidin-3-yl)-1H-pyrazolo[3,4-d]pyrimidin-4-amine (64.8 mg, 0.168 mmol, prepared as described in *Org. Biomol. Chem.*, 2015, 13, 5147-5157) and DIPEA (0.133 mL, 0.763 mmol) in DMF (1 mL) was added HATU (69.6 mg, 0.183 mmol) and the mixture stirred at rt for 1 h. The reaction mixture was directly loaded onto a reverse phase (C18) cartridge (30 g) and eluted with a 45-95% acetonitrile-water (ammonium carbonate modifier) gradient, however the product failed to elute. The column was flushed with MeOH and the eluent evaporated in vacuo, then the residue partitioned between DCM (20 mL) and water (20 mL) and the phases separated using a hydrophobic frit. The organic layer was concentrated under a stream of nitrogen to give the title compound (130 mg) in 80% purity (by LCMS) as an orange solid. LCMS: RT=1.39 mins, [(M+2H)/2]=670.4 (80% pure).

Example 1

(S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide, 2Hydrochloride

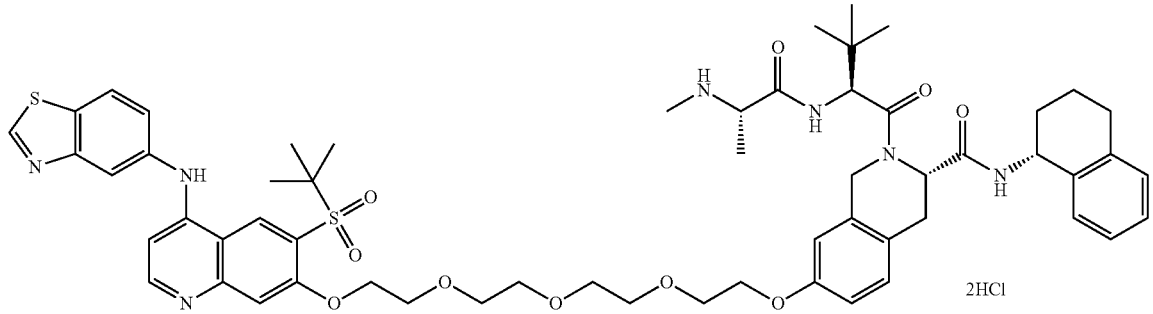 [SMILES: CN[C@@H](C)C(=O)N[C@H](C(=O)N1Cc2cc(OCCOCCOCCOCCOc3cc4nccc(Nc5ccc6scnc6c5)c4cc3S(=O)(=O)C(C)(C)C)ccc2C[C@H]1C(=O)N[C@@H]1CCCc2ccccc21)C(C)(C)C]

A solution of tert-butyl ((S)-1-(((S)-1-((S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (65 mg, 0.055 mmol) in THF (1.5 mL) was treated with hydrochloric acid (4M in 1,4-dioxane) (3 mL, 12.00 mmol) and allowed to stand overnight. The solution was evaporated to dryness and the residual product was subjected to purification by mass-directed automated preparative HPLC (ammonium bicarbonate modifier). The recovered material was dissolved in THF (1 mL), treated with 1M HCl in 1,4-dioxane (0.5 mL), evaporated and dried under vacuum to afford the title compound (45 mg, 0.039 mmol, 71% yield). LCMS RT=0.72 min, ES+ve 1093.

Example 2

(S)-7-(2-(2-(2-(2-((4-(Benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((S)-1,2,3,4-tetrahydronaphthalen-1-yl)-1,2,3,4-tetrahydroisoquinoline-3-carboxamide, 2Hydrochloride

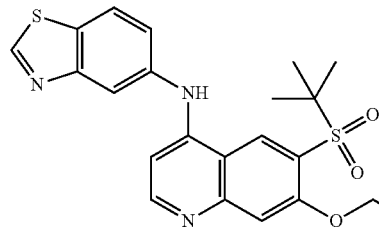
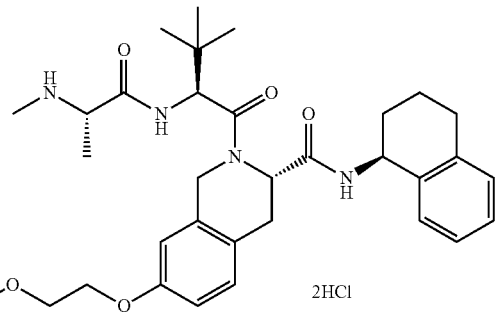

2HCl (S)-7-(2-(2-(2-(2-((4-(Benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((S)-1,2,3,4-tetrahydronaphthalen-1-yl)-1,2,3,4-tetrahydroisoquinoline-3-carboxamide, 2Hydrochloride was prepared in a method analogous to that for (S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide, 2Hydrochloride (Example 1) using (S)-1,2,3,4-tetrahydronaphthalen-1-amine in place of (R)-1,2,3,4-tetrahydronaphthalen-1-amine. LCMS RT=0.74 min, ES+ve 1093.

Example 3

(S)-2-((S)-3,3-Dimethyl-2-((S)-2-(methylamino)propanamido)butanoyl)-7-(2-(2-(2-(2-(4-((6-hydroxy-2-(4-hydroxyphenyl)benzo[b]thiophen-3-yl)oxy)phenoxy)ethoxy)ethoxy)ethoxy)ethoxy)-N—((R)-1,2,3,4-tetrahydronaphthalen-1-yl)-1,2,3,4-tetrahydroisoquinoline-3-carboxamide

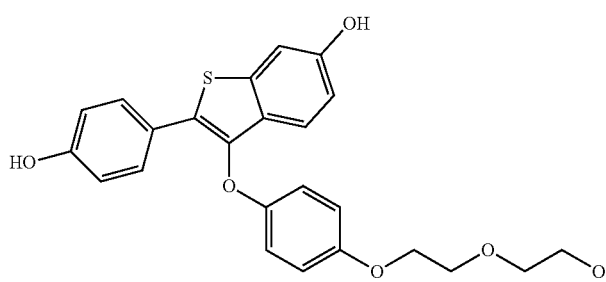
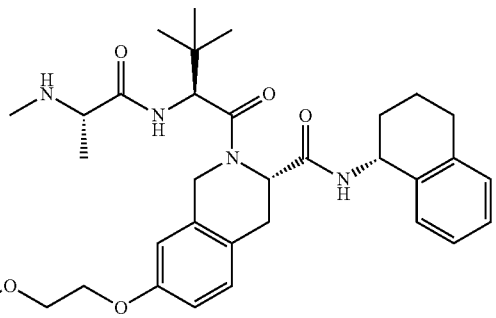

A solution of tert-butyl ((S)-1-(((S)-1-((S)-7-(2-(2-(2-(2-(4-((6-(benzyloxy)-2-(4-(benzyloxy)phenyl)benzo[b]thiophen-3-yl)oxy)phenoxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (18 mg, 0.014 mmol) in a mixture of ethanol (2 mL) and THF (2 mL) was added to palladium on carbon (20 mg, 0.19 mmol) and stirred in an atmosphere of hydrogen for 5 hours. The mixture was filtered and the filtrate was evaporated to dryness. The residue was dissolved in 1 mL of THF and treated with 4M HCl in 1,4-dioxane (2 mL, 8 mmol). After 2 hours the mixture was evaporated to dryness and the product was subjected to purification by mass-directed automated preparative HPLC (formic acid modifier) to afford the title compound (5.3 mg, 5 μmol, 36% yield). LCMS RT (Method B)=1.36 min, ES+ve 1030

Example 4

(2S,4S)-4-(14-(4-(4-((R)-3-(4-Amino-3-(4-phenoxyphenyl)-1H-pyrazolo[3,4-d]pyrimidin-1-yl)piperidin-1-yl)-4-oxobutyl)piperazin-1-yl)-3,6,9,12-tetraoxatetradecanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide

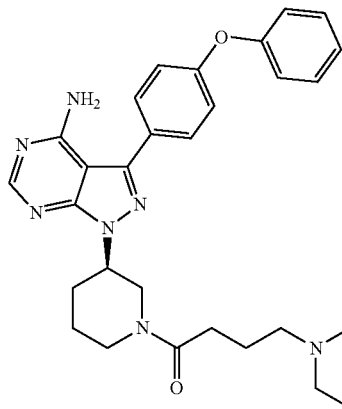
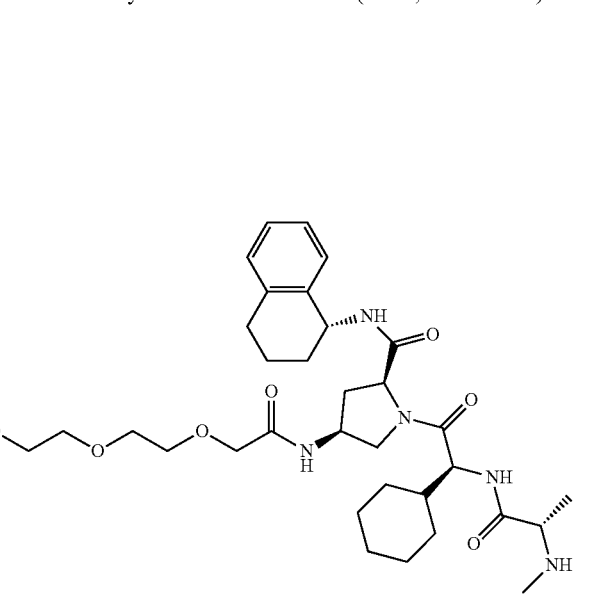

A solution of tert-butyl ((S)-1-(((S)-2-((2S,4S)-4-(14-(4-((E)-4-((R)-3-(4-amino-3-(4-phenoxyphenyl)-1H-pyrazolo[3,4-d]pyrimidin-1-yl)piperidin-1-yl)-4-oxobut-2-en-1-yl)piperazin-1-yl)-3,6,9,12-tetraoxatetradecanamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)methyl)carbamate (50 mg, 0.030 mmol) and Pd/C (10% w/w, 32 mg, 0.030 mmol) in EtOH (2 mL) was stirred under an atmosphere of hydrogen for 3 h. The reaction mixture was passed through a pad of Celite, then the pad washed with MeOH and the solution evaporated in vacuo.

The residue was directly dissolved in DCM (5 mL) then TFA (1 mL) was added and the mixture stirred at rt for 1 h. The mixture was evaporated in vacuo, then dissolved in minimal MeOH and purified by MDAP (ammonium carbonate modifier gradient). The appropriate fractions were combined and dried under a stream of nitrogen to give the title compound, 15 mg as a white solid. LCMS: RT=1.25 mins, ES+=1240.7

Western Blot Quantification of RIP2 Levels in THP1 Cells

Compounds were tested in THP1 cells (acute myeloid leukaemia—BioCat 106491) and the effect on RIP2 protein levels were assessed by Western blotting. For each sample $7.5 \times 10^6$ cells were resuspended in media containing the indicated concentrations of PROTAC and incubated 37° C. and 5% $CO_2$ overnight. The following day, cells were harvested, and the total amount of protein was quantified using the Pierce™ BCA Protein Assay kit (Thermo Scientific, 23227). 25 μg of total protein were separated on a polyacrylamide Bis-Tris gel at constant voltage and further transfered onto PVDF membranes (Millipore, IPFL00010). Membranes were blocked against non-specific binding with Odyssey blocking buffer (Licor, 927-40000) for 1 hour at room temperature, then incubated with the primary antibodies rabbit anti-RIPK2 (Cell Signaling, 4142) oevrnight at 4° C. Next day the mouse anti-actin (Sigma, A2228) at a 1:20 000 dilution was added and the membranes were further incubated for 2 hours at room temperature. Membranes were washed 3 times with PBS+0.1% Tween 20 then incubated with donkey anti-mouse 800CW (Licor, 926-32212) and donkey anti-mouse IRdye 680RD (Licor, 926-68072) diluted 1:5 000 in Odyssey blocking buffer+0.1% Tween 20+0.01% SDS, 1 hour at room temperature, followed by washing in PBS+0.1% Tween 20. The infrared signal was detected using an Odyssey scanner (Licor Biosciences) and densitometry was performed using the Odyssey 2.1 Analyser software (Licor Biosciences).

RIPK2 degradation was expressed relative to the DMSO only treated sample RIP2 Protacs displayed >80% degradation of RIP2 at concentrations <1 uM.

Western Blot Quantification of BTK Levels in THP1 Cells

Compounds were assessed in an analogous manner to that described for RIP2 above using the following andibodies:

Primary antibody: BTK (D3HS) Rabbit mAb (Cell Signalling; #8547; Lot #0005) in 1:1000 dilution.

Loading control tubulin mouse primary antibody: Monoclonal anti-β-tubulin antibody mouse (Sigma-Aldrich, T8328; Lot #094M4810V)—1:10,000.

Secondary Antibodies: Donkey anti-rabbit 800CW (Licor; #926-32213)

Donkey anti-mouse 680CW (Licor; #926-68072)

BTK Protacs displayed >80% degradation of BTK at concentrations <1 uM.

Western Blot Quantification of ERa Levels in MCF-7 Cells

Compounds were assessed in an analogous manner to that described for RIP2 above using the following andibodies:

Primary antibodies: rabbit anti-ERα (Bethyl, 498) or rabbit anti-ERα (Santa Cruz, sc-543), Loading control actin mouse antibody: Monoclonal mouse anti-actin (Sigma, A2228).

Secondary antibodies: donkey anti-rabbit IRdye 800CW (Licor, 926-32213), donkey anti-mouse IRdye 680RD (Licor, 926-68072).

ERa Protacs displayed >50% degradation of ERa at concentrations <1 uM

The invention claimed is:

1. A compound selected from the group consisting of
(S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide, (S)-7-(2-(2-(2-(2-((4-(Benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N—((S)-1,2,3,4-tetrahydronaphthalen-1-yl)-1,2,3,4-tetrahydroisoquinoline-3-carboxamide, (S)-2-((S)-3,3-Dimethyl-2-((S)-2-(methylamino)propanamido)butanoyl)-7-(2-(2-(2-(2-(4-((6-hydroxy-2-(4-hydroxyphenyl)benzo[b]thiophen-3-yl)oxy)phenoxy)ethoxy)ethoxy)ethoxy)ethoxy)-N—((R)-1,2,3,4-tetrahydronaphthalen-1-yl)-1,2,3,4-tetrahydroisoquinoline-3-carboxamide, and (2S,4S)-4-(14-(4-(4-((R)-3-(4-Amino-3-(4-phenoxyphenyl)-1H-pyrazolo[3,4-d]pyrimidin-1-yl)piperidin-1-yl)-4-oxobutyl)piperazin-1-yl)-3,6,9,12-tetraoxatetradecanamido)-1-((S)-2-cyclohexyl-2-((S)-2-(methylamino)propanamido)acetyl)-N—((R)-1,2,3,4-tetrahydronaphthalen-1-yl)pyrrolidine-2-carboxamide, or a pharmaceutically acceptable salt thereof.

2. A pharmaceutical composition comprising a compound of formula (I) according to claim 1 or a pharmaceutically acceptable salt thereof and one or more of pharmaceutically acceptable carriers, diluents and excipients.

* * * * *